(12) United States Patent
Medema et al.

(10) Patent No.: US 11,000,692 B2
(45) Date of Patent: *May 11, 2021

(54) WEARABLE CARDIOVERTER DEFIBRILLATOR (WCD) SYSTEM WITH ISOLATED PATIENT PARAMETER COMPONENT

(71) Applicant: West Affum Holdings Corp., Grand Cayman (KY)

(72) Inventors: Douglas Keith Medema, Everett, WA (US); Kenneth Frederick Cowan, Redmond, WA (US); Zhong Qun Lu, Everett, WA (US)

(73) Assignee: West Affum Holdings Corp., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 16/442,523

(22) Filed: Jun. 16, 2019

(65) Prior Publication Data

US 2019/0366111 A1    Dec. 5, 2019

Related U.S. Application Data

(63) Continuation of application No. 15/365,801, filed on Nov. 30, 2016, now Pat. No. 10,322,291.

(Continued)

(51) Int. Cl.
*A61N 1/39* (2006.01)
*A61N 1/04* (2006.01)

(52) U.S. Cl.
CPC ........... *A61N 1/3987* (2013.01); *A61N 1/046* (2013.01); *A61N 1/0484* (2013.01); *A61N 1/3925* (2013.01); *A61N 1/3975* (2013.01)

(58) Field of Classification Search
CPC ...... A61N 1/39; A61N 1/3904; A61N 1/3925; A61N 1/3975; A61N 1/3981
See application file for complete search history.

(56) References Cited

U.S. PATENT DOCUMENTS 3,724,355 A   4/1973   Busch et al.
4,583,524 A   4/1986   Hutchins
(Continued)

FOREIGN PATENT DOCUMENTS

| CA | 2942933 A1 | 8/2015 |
|---|---|---|
| CN | 103405851 A | 11/2013 |
| WO | 9839061 A2 | 9/1998 |

OTHER PUBLICATIONS

European Search Report of European Application 16202067. 9 pages, dated Apr. 25, 2017.

(Continued)

*Primary Examiner* — George R Evanisko
(74) *Attorney, Agent, or Firm* — Spectrum IP Law Group LLC

(57) ABSTRACT

Embodiments are directed to wearable cardioverter defibrillator (WCD) systems that include patient parameter electrodes, such as ECG electrodes, that are at least substantially electrically isolated from other circuits of the WCD system. In embodiments, the WCD system includes a power source, an energy storage module, and a processor each connected to a first circuit ground. A patient parameter sense port, such as an ECG port, is coupled to the patient. A measurement circuit may render a physiological input from the sensed patient parameter received at the patient parameter sense port, and the measurement circuit includes an isolating circuit that electrically isolates the patient parameter sense port from the first circuit ground. The sensing of physiologi- (Continued)

*SAMPLE COMPONENTS* cal inputs of the patient can be improved, resulting in fewer erroneous readings and false alarms.

13 Claims, 6 Drawing Sheets

Related U.S. Application Data

(60) Provisional application No. 62/263,566, filed on Dec. 4, 2015.

(56) References Cited

U.S. PATENT DOCUMENTS

| | | | |
|---|---|---|---|
| 4,619,265 A | 10/1986 | Morgan et al. | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bomn et al. | |
| 5,353,793 A | 10/1994 | Bomn | |
| RE34,800 E | 11/1994 | Hutchins | |
| 5,394,892 A | 3/1995 | Kenny et al. | |
| 5,405,362 A | 4/1995 | Kramer et al. | |
| 5,474,574 A | 12/1995 | Payne et al. | |
| 5,554,174 A | 9/1996 | Causey, III | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder et al. | |
| 6,427,083 B1 | 7/2002 | Owen et al. | |
| 6,437,083 B1 | 8/2002 | Brack et al. | |
| 6,529,875 B1 | 3/2003 | Nakajima et al. | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,089,685 B2 | 7/2015 | Sullivan et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,454,219 B2 | 9/2016 | Volpe et al. | |
| 9,592,403 B2 | 3/2017 | Sullivan | |
| 10,322,291 B2* | 6/2019 | Medema | A61N 1/3682 |
| 2011/0022105 A9 | 1/2003 | Owen et al. | |
| 2003/0158593 A1 | 8/2003 | Heilman et al. | |
| 2004/0049117 A1 | 3/2004 | Ideker et al. | |
| 2005/0107833 A1 | 5/2005 | Freeman et al. | |
| 2005/0107834 A1 | 5/2005 | Freeman et al. | |
| 2008/0312709 A1 | 12/2008 | Volpe et al. | |
| 2009/0005827 A1 | 1/2009 | Weintraub et al. | |
| 2010/0007413 A1 | 1/2010 | Herleikson et al. | |
| 2010/0114248 A1* | 5/2010 | Donofrio | A61N 1/39624 |
| | | | 607/60 |
| 2010/0298899 A1 | 11/2010 | Donnelly et al. | |
| 2011/0288604 A1 | 11/2011 | Kaib et al. | |
| 2011/0288605 A1 | 11/2011 | Kaib et al. | |
| 2012/0022355 A1 | 1/2012 | Byrd et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0231711 A1 | 9/2013 | Kaib et al. | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0025131 A1 | 1/2014 | Sullivan et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0037636 A1 | 2/2015 | Amsler et al. | |
| 2015/0039053 A1 | 2/2015 | Kaib et al. | |
| 2015/0328472 A1 | 11/2015 | Sullivan et al. | |
| 2016/0004831 A1 | 1/2016 | Carlson et al. | |
| 2016/0082277 A1 | 3/2016 | Foshee, Jr. et al. | |
| 2017/0056682 A1* | 3/2017 | Kumar | G16H 50/20 |

OTHER PUBLICATIONS

Heartstart MRx and XL AED Algorithm—Application Note, Jul. 2001, Edition 2 Philips Healthcare, USA.
Klein, H. U., Goldenberg L, & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.
Lifecor LifeVest System Model WCD 3100 Operator's Manual, 2006, PN 20B0040 Rev FI, Zoll Lifecor Corporation, Pittsburgh, PA.
LifeVest Model 4000 Patient Manual, Zoll, 2009, PN 20B0047 Rev B.
The LifeVest Network/Patient Data Management System, Zoll, 2015, 20C0503 Rev A.
First Office action and Search Report dated Aug. 30, 2018, to CN Patent Application No. 2016111063501.
Second Office Action dated May 18, 2020, to CN Patent Application No. 2016111106350.1.
Pagan-Carlo, et al., "Encircling Overlapping Multipulse Shock Waveforms for Transthoracic Defibrillation," JACC Journals, Dec. 1998, vol. 32 Issue 7, p. 2065-2071.

* cited by examiner

SAMPLE COMPONENTS OF WEARABLE
CARDIOVERTER DEFIBRILLATOR (WCD) SYSTEM

*SAMPLE COMPONENTS OF EXTERNAL DEFIBRILLATOR*

*SAMPLE COMPONENTS OF ISOLATING CIRCUIT*

SAMPLES OF COMPONENTS OF THE ISOLATING CIRCUIT

WEARABLE CARDIOVERTER DEFIBRILLATOR (WCD) SYSTEM WITH ISOLATED PATIENT PARAMETER COMPONENT

CROSS REFERENCE TO RELATED APPLICATIONS

The present application is a continuation of U.S. application Ser. No. 15/365,801 filed Nov. 30, 2016, which in turn claims the benefit of U.S. Provisional Application No. 62/263,566 filed Dec. 4, 2015. Said application Ser. No. 15/365,801 and said Application No. 62/263,566 are hereby incorporated by reference in their entireties.

BACKGROUND

When people suffer from some types of heart arrhythmias, the result may be that blood flow to various parts of the body is reduced. Some arrhythmias may even result in a sudden cardiac arrest (SCA). SCA can lead to death very quickly, e.g. within 10 minutes, unless treated in the interim.

Some people have an increased risk of SCA. People at a higher risk include patients who have had a heart attack, or a prior SCA episode. A frequent recommendation is for these people to receive an implantable cardioverter defibrillator (ICD). The ICD is surgically implanted in the chest, and continuously monitors the patient's electrocardiogram (ECG). If certain types of heart arrhythmias are detected, then the ICD delivers an electric shock through the heart.

After being identified as having an increased risk of an SCA, and before receiving an ICD, these people are sometimes given a wearable cardioverter defibrillator (WCD) system. (Early versions of such systems were called wearable cardiac defibrillator (WCD) systems.) A WCD system typically includes a harness, vest, or other garment that the patient is to wear. The WCD system includes a defibrillator and electrodes, coupled to the harness, vest, or other garment. When the patient wears the WCD system, the external electrodes may then make good electrical contact with the patient's skin, and therefore can help determine the patient's ECG. If a shockable heart arrhythmia is detected, then the defibrillator delivers the appropriate electric shock through the patient's body, and thus through the heart.

BRIEF SUMMARY

The present description gives instances of wearable cardiac defibrillator (WCD) systems, the use of which may help overcome problems and limitations of the prior art.

In particular, embodiments are directed to WCD systems that include patient parameter electrodes, such as ECG electrodes, which are at least substantially electrically isolated from other circuits of the wearable cardioverter defibrillator (WCD) system by using separate grounds and optionally an isolating circuit.

An advantage over the prior art is that the sensing of a physiological input of the patient may be improved, resulting in fewer erroneous readings and false alarms.

These and other features and advantages of the claimed invention will become more readily apparent in view of the embodiments described and illustrated in the present disclosure, namely from the present written specification and the drawings.

DETAILED DESCRIPTION

As has been mentioned, the present description is about wearable cardioverter defibrillator (WCD) systems. Embodiments are now described in more detail.

A WCD system made according to embodiments has a number of components. These components can be provided separately as modules that can be interconnected, or can be combined with other components, etc.

A component of a WCD system can be a support structure, which is configured to be worn by the patient. The support structure can be any structure suitable for wearing, such as a harness, a vest, a half-vest—for example over the left side of the torso that positions electrodes on opposite sides of the heart, one or more belts that are configured to be worn horizontally or possibly vertically over a shoulder, another garment, and so on. The support structure can be implemented in a single component or multiple components. For example, a support structure may have a top component resting on the shoulders, for ensuring that the defibrillation electrodes will be in the appropriate positions for defibrillating, and a bottom component resting on the hips, for carrying the bulk of the weight of the defibrillator. A single component embodiment could be with a belt around at least the torso. Other embodiments could use an adhesive material or another way for attaching to the patient, without encircling any part of the body. There can be other examples.

Figure 1:
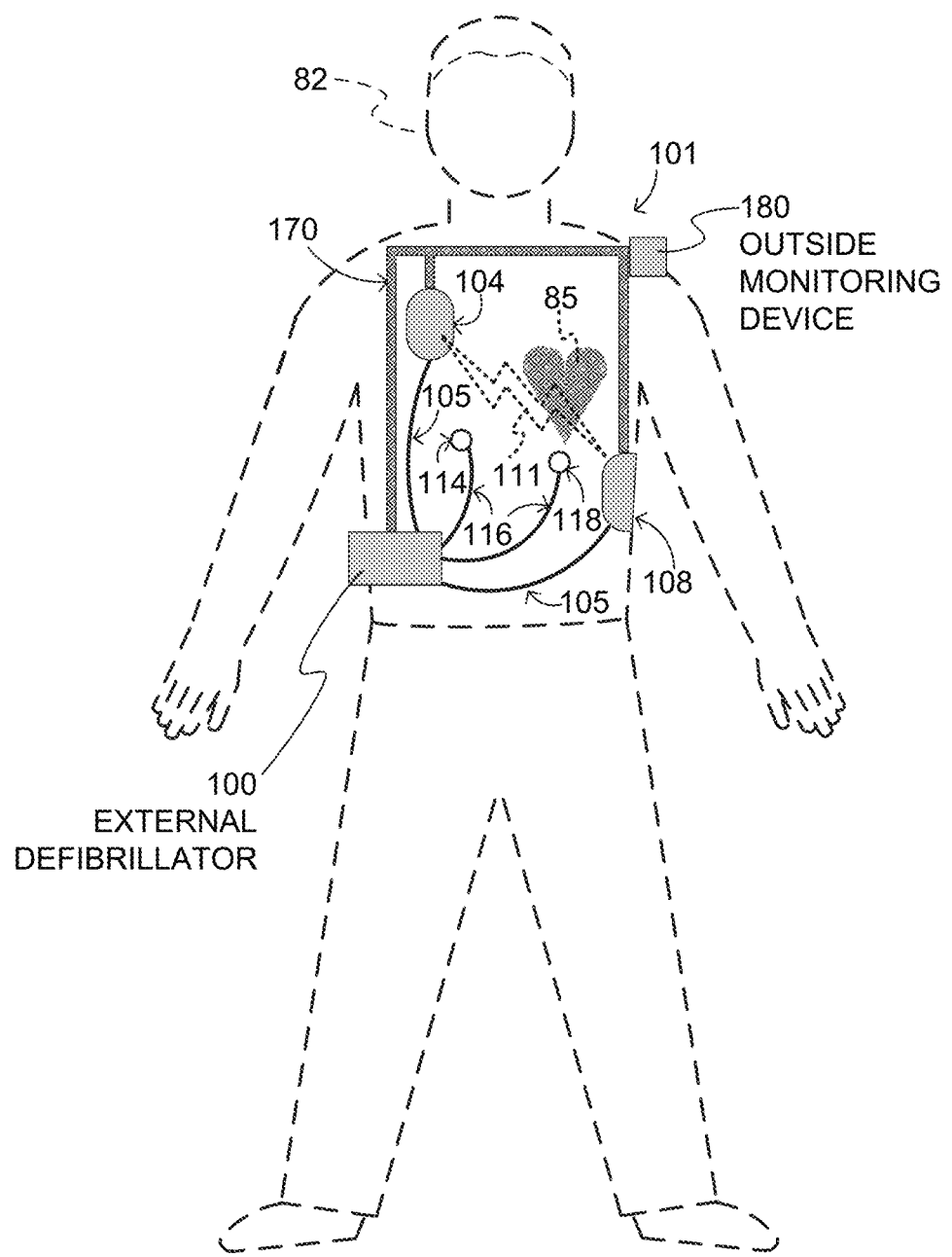
FIG. 1 is a diagram of components of a sample wearable cardioverter defibrillator (WCD) system, made according to embodiments.

FIG. 1 depicts components of a WCD system 101 made according to embodiments, as it might be worn by a patient 82. A patient such as patient 82 may also be referred to as a person and/or wearer, since that patient wears components of the WCD system.

In FIG. 1, a generic support structure 170 is shown relative to the body of patient 82, and thus also relative to his or her heart 85. Structure 170 could be a harness, a vest, a half-vest, one or more belts, or a garment, etc., as per the above. Structure 170 could be implemented in a single component, or multiple components, and so on. Structure 170 is wearable by patient 82, but the manner of wearing it is not depicted, as structure 170 is depicted only generically in FIG. 1 and, in fact, partly conceptually.

A WCD system according to embodiments is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 are coupled to support structure 170. As such, many of the components of defibrillator 100 can be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111, also known as a defibrillation shock or therapy shock, is intended to go through and restart heart 85, in an effort to save the life of patient 82. Pulse 111 can further include one or more pacing pulses, and so on.

A prior art defibrillator typically decides whether to defibrillate or not based on an ECG signal of the patient. However, defibrillator 100 can defibrillate, or not defibrillate, also based on other inputs.

In this embodiment, WCD system 101 includes patient parameter electrodes 114 and 118 coupled to external defibrillator 100 via electrode leads 116. Patient parameter electrodes 114 and 118 are shown unsupported by support structure 170. Patient parameter electrodes may alternatively be supported by support structure 170 as appropriate for the patent parameter being monitored. In some embodiments there may be only one patient parameter electrode or more than two patient parameter electrodes, as appropriate for the patient parameter or parameters being monitored. In an embodiment in which the patient parameter electrodes include ECG electrodes, for example, there may be a required number of patient parameter electrodes depending on the configuration being used, such as three, four, five, or ten electrodes, which are distributed appropriately on the patient's body, as is known in the art. Patient parameter electrodes 114 and 118 are therefore intended as representative of a set of electrodes that is appropriate for the parameter or parameters being monitored.

The WCD system may optionally include an outside monitoring device 180. Device 180 is called an "outside" device because it is provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document. Device 180 may include one or more transducers that are configured to render one or more physiological inputs from one or more patient parameters that it senses.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this disclosure.

Figure 2:
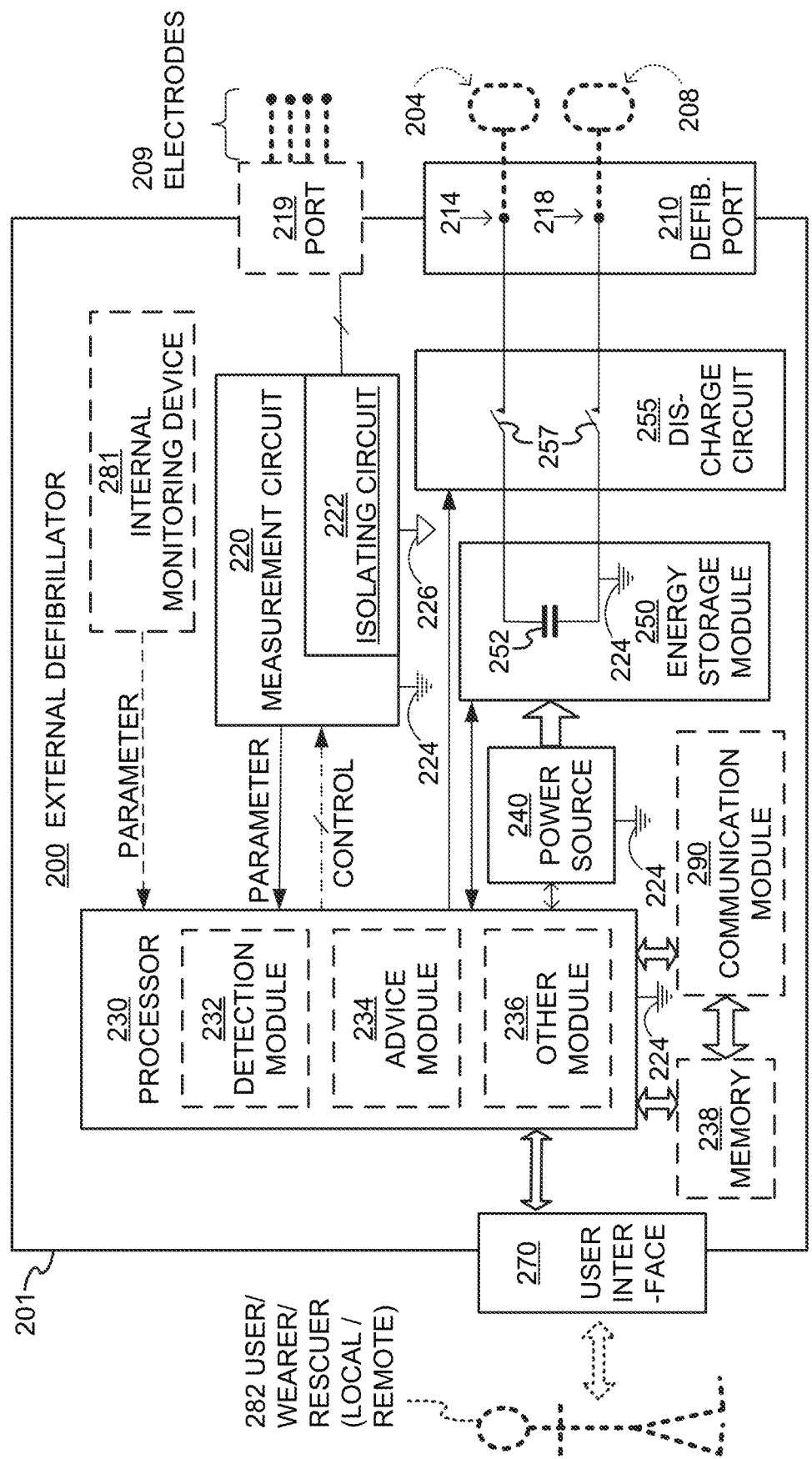
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which is also known as casing 201.

External defibrillator 200 is intended for a patient who would be wearing it, such as patient 82 of FIG. 1. Defibrillator 200 may further include a user interface 270 for a user 282. User 282 can be patient 82, also known as wearer 82. Or user 282 can be a local rescuer at the scene, such as a bystander who might offer assistance, or a trained person. Or, user 282 might be a remotely located trained caregiver in communication with WCD system 101.

User interface 270 can be made in any number of ways. User interface 270 may include output devices, which can be visual, audible or tactile, for communicating to a user. For example, an output device can be a light, or a screen to display what is sensed, detected and/or measured, and provide visual feedback to rescuer 282 for their resuscitation attempts, and so on. Another output device can be a speaker, which can be configured to issue voice prompts, etc. Sounds, images, vibrations, and anything that can be perceived by user 282 can also be called human perceptible indications. User interface 270 may also include input devices for receiving inputs from users. Such input devices may additionally include various controls, such as pushbuttons, keyboards, touchscreens, a microphone, and so on. An input device can be a cancel switch, which is sometimes called a "live-man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In embodiments where electrodes are used on the patient in association with monitoring device 281 (or an external monitoring device such as outside monitoring device 180 of FIG. 1), such as electrodes 114 and 118 illustrated in FIG. 1, then the associated monitoring device may also have an isolating circuit as discussed below with reference to measurement circuit 220. Internal monitoring device 281 can be complementary or an alternative to outside monitoring device 180 of FIG. 1. Allocating which of the system parameters are to be monitored by which monitoring device can be done according to design considerations. Device 281 may include one or more transducers that are configured to render one or more physiological inputs from one or more patient parameters that it senses.

Patient physiological parameters include, for example, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, the monitoring device could include a perfusion sensor, a pulse oximeter, a Doppler device for detecting blood flow, a cuff for detecting blood pressure, an optical sensor, illumination detectors and perhaps sources for detecting color change in tissue, a motion sensor, a device that can detect heart wall movement, a sound sensor, a device with a microphone, an SpO2 sensor, and so on. Pulse detection is taught at least in Physio-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 82. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2 or CO2; f) respiratory function, respiratory rate, etc.; g) motion, level of activity; and so on. Once a trend is detected, it can be stored and/or reported via a communication link, along perhaps with a warning. From the report, a physician monitoring the progress of patient 82 will know about a condition that is either not improving or deteriorating.

Patient state parameters include recorded aspects of patient 82, such as motion, posture, whether they have spoken recently plus maybe also what they said, and so on, plus optionally the history of these parameters. Or, one of these monitoring devices could include a location sensor such as a global positioning system (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be configured to detect a motion event. In response, the motion detector may render or generate from the detected motion event a motion detection input that can be received by a subsequent device or functionality. A motion event can be defined as is convenient, for example a change in motion from a baseline motion or rest, etc. Such a motion detector can be made in many ways as is known in the art, for example by using an accelerometer. In such cases, the patient parameter is a motion, the transducer includes a motion detector, and the physiological input is a motion measurement.

System parameters of a WCD system can include system identification, battery status, system date and time, reports of self-testing, records of data entered, records of episodes and intervention, and so on.

Environmental parameters can include ambient temperature and pressure. A humidity sensor may provide information as to whether it is likely raining. Presumed patient location could also be considered an environmental parameter. The patient location could be presumed if monitoring device 180 or 281 includes a GPS location sensor as per the above.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in energy storage module 250. The electric charge will be the shock for defibrillation, pacing, and so on.

Defibrillator 200 may optionally also have a patient parameter sense port 219 in housing 201 and configured to be coupled to the patient, such as for plugging in sensing electrodes 209. In some embodiments, patient parameter port 219 is an ECG port, in which case sensing electrodes 209 are ECG electrodes having ECG leads connecting the electrodes to the port. It is also possible that sensing electrodes 209 can be connected continuously to patient parameter port 219, instead. Sensing electrodes 209 are types of transducers that can help sense a patient parameter signal, such as a voltage. In embodiments in which the sensing port is an ECG port, sensing electrodes 209 sense an ECG signal, e.g. a 12-lead signal, or a signal from a different number of leads, especially if they make good electrical contact with the body of the patient. Sensing electrodes 209 can be attached to the inside of support structure 170 for making good electrical contact with the patient, similarly as defibrillation electrodes 204, 208.

In some embodiments, defibrillator 200 also includes a transducer that includes a measurement circuit 220. Measurement circuit 220 senses one or more electrical physiological signal of the patient from patient parameter sense port 219. The parameter can be an ECG, which can be sensed as a voltage difference between sensing electrodes 209. In addition, the parameter can be an impedance, which can be sensed between separate sensing electrodes 209 connected to measurement circuit 220 through the connections of patient parameter sense port 219. Sensing the impedance can be useful for detecting, among other things, whether sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

In some embodiments, measurement circuit 220 includes an isolating circuit 222 configured to electrically isolate patient parameter sense port 219 from a first circuit ground 224 to which other external defibrillator circuits are connected. Isolating circuit 222 may in turn use a second circuit ground 226 isolated from first circuit ground 224 for circuits electrically coupled to sense port 219. This isolation improves the quality of the acquired ECG data, which may result in fewer false alarms and improved patient safety. This is an improvement over prior art versions that use a common voltage reference, typically referred to as a "ground," for all parts of the WCD system, which is therefore not isolated. Non-isolated ECG acquisition systems are susceptible to environmental noise sources such as 60 Hz fields in the vicinity of the WCD system. Patient leakage currents could be difficult to control. Further, electrical noise generated by switch mode power supplies or high voltage charging circuits could couple into the ECG acquisition system of the WCD system.

Defibrillator 200 also includes a processor 230 connected to first circuit ground 224. Processor 230 may be implemented in any number of ways. Such ways include, by way of example and not of limitation, digital and/or analog processors such as microprocessors and digital signal processors (DSPs); controllers such as microcontrollers; software running in a machine; programmable circuits such as field programmable gate arrays (FPGAs), field-programmable analog arrays (FPAAs), programmable logic devices (PLDs), application specific integrated circuits (ASICs), any combination of one or more of these, and so on.

Processor 230 can be considered to have a number of modules. One such module can be a detection module 232. Detection module 232 can include a ventricular fibrillation (VF) detector. The patient's sensed ECG from measurement circuit 220, which can be available as physiological inputs, data, or other signals, may be used by the VF detector to determine whether the patient is experiencing VF. Detecting VF is useful, because VF results in SCA. Detection module 232 can also include a (shockable) ventricular tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more of ECG signals that are captured according to embodiments, and determining whether a shock criterion is met. The determination can be made from a rhythm analysis of the captured ECG signal or otherwise.

In some embodiments, when the determination is to shock, an electrical charge is delivered to the patient. Delivering the electrical charge is also known as discharging. Shocking can be for defibrillation, pacing, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in any number of ways. Such ways include, by way of example and not of limitation, volatile memories, nonvolatile memories (NVM), read-only memories (ROM), random access memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, processes, actions and/or methods to be performed, and/or the processor to cause other devices or components or blocks to perform such functions, processes, actions and/or methods. The programs can be operational for the inherent needs of processor 230 and can also include protocols and ways that decisions can be made by advice module 234. In addition, memory 238 can store prompts for user 282, if this user is a local rescuer, or the patient. Moreover, memory 238 can store data. The data can include patient data, system data and environmental data, for example as learned by internal monitoring device 281 and outside monitoring device 180. The data can be stored in memory 238 before it is transmitted out of defibrillator 200 or stored there after it is received by defibrillator 200.

Defibrillator 200 may also include a power source 240 also connected to first circuit ground 224. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an energy storage capacitor, and so on. In some embodiments, power source 240 is controlled by processor 230.

Defibrillator 200 additionally includes an energy storage module 250 also connected to first circuit ground 224. Energy storage module can be coupled to the support structure of the WCD system. Module 250 is where some electrical energy is stored in the form of an electrical charge, when preparing it for discharge to administer a shock. Module 250 can be charged from power source 240 to the right amount of energy, as controlled by processor 230. In typical implementations, module 250 includes a capacitor 252, which can be a single capacitor or a system of capacitors, and so on. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 270.

Defibrillator 200 can optionally include a communication module 290, for establishing one or more wireless communication links with other devices of other entities, such as a remote assistance center, Emergency Medical Services (EMS), and so on. Module 290 may also include an antenna, portions of a processor, and other sub-components as may be deemed necessary by a person skilled in the art. This way, data and commands can be communicated, such as patient data, event information, therapy attempted, CPR performance, system data, environmental data, and so on.

Defibrillator 200 can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since bodies behave differently. For example, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

Figure 3:
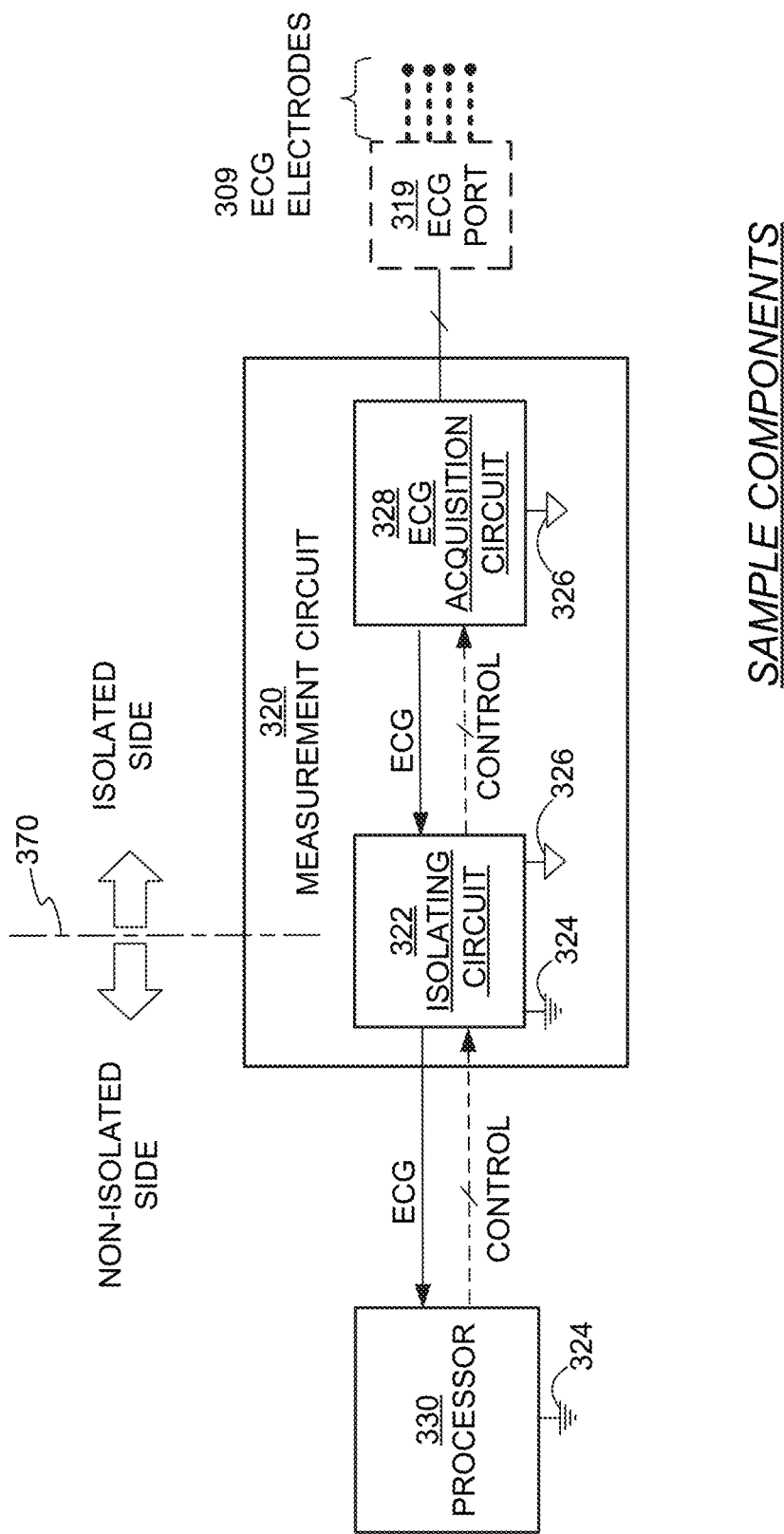
FIG. 3 is a block diagram of a sample of a measurement circuit of the external defibrillator of FIG. 2, made according to embodiments.

FIG. 3 illustrates samples of components of a measurement circuit 320. Measurement circuit 320 is an embodiment of measurement circuit 220 of FIG. 2 that includes an isolating circuit 322 and an ECG acquisition circuit 328. In this embodiment, the patient parameter is an electrical patient physiological signal, e.g., an ECG signal, received at an ECG port 319, as an example of patient parameter sense port 219, from Electrocardiogram (ECG) electrodes 309, as an example of patient parameter electrodes 209. The physiological input thus includes an ECG signal acquired by the ECG electrodes. ECG acquisition circuit 328 is configured to detect the ECG signal. ECG acquisition circuit 328 is operatively coupled to the patient parameter sense port (ECG port 319) and isolating circuit 322. ECG acquisition circuit 328 operatively couples isolating circuit 322 to ECG port 319, a patient parameter sense port, and correspondingly to ECG electrodes 309. ECG acquisition circuit 328 is connected to second circuit ground 326 and is isolated from first circuit ground 324. Isolating circuit 322 can be thought of defining an isolation boundary 370, which separates an isolated side from a non-isolated side in the WCD system. As will be seen later in this document, isolation boundary 370 may be implemented by an isolation barrier.

Measurement circuit 320 has a second circuit ground 326 that is isolated from first circuit ground 324. Isolating circuit 322 is configured to electrically isolate first circuit ground 324 from second circuit ground 326, and thereby electrically isolate ECG port 319, as an example of a patient parameter sense port, from first circuit ground 324. Processor 330, as an example of processor 230, is electrically connected to first circuit ground 324 and received ECG data from the portion of isolating circuit 322 also connected to first circuit ground 324. Optionally, processor 330 may send one or more control signals to ECG acquisition circuit 328 via isolating circuit 322.

Figure 4:
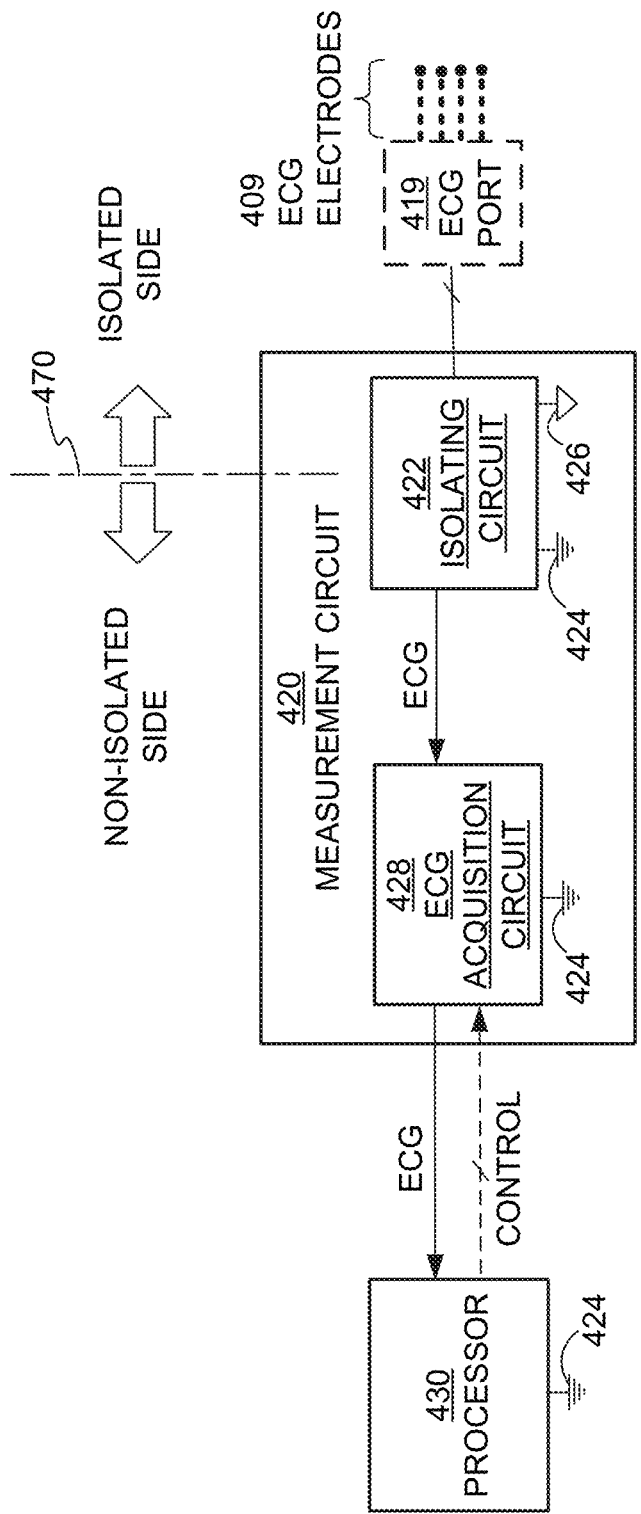
FIG. 4 is a block diagram of a sample of a measurement circuit of the external defibrillator of FIG. 2, made according to alternate embodiments.

FIG. 4 is a block diagram of a sample of a measurement circuit of the external defibrillator of FIG. 2, made according to alternate embodiments. Measurement circuit 420 includes an isolating circuit 422 and an ECG acquisition circuit 428. In this embodiment, an ECG port 419 receives a patient-parameter ECG signal from ECG electrodes 409. ECG acquisition circuit 428 is configured to detect the ECG signal. Isolating circuit 422 is operatively coupled to ECG port 419 and ECG acquisition circuit 428. Isolating circuit 422 operatively couples ECG acquisition circuit 428 to ECG port 419, the patient parameter sense port. In this embodiment, ECG acquisition circuit 428 is connected to the first circuit ground, and isolating circuit 422 of measurement circuit 420 has a portion connected to first circuit ground 424 and a portion connected to second circuit ground 426, which is isolated from the first circuit ground.

Isolating circuit 422 is configured to electrically isolate first circuit ground 424 from second circuit ground 426, and thereby electrically isolate ECG port 419, and thereby ECG electrodes 409, from first circuit ground 424. Processor 430, as an example of processor 230, is electrically connected to first circuit ground 324 and receives ECG data directly from ECG acquisition circuit 428. Optionally, processor 430 may send one or more control signals to ECG acquisition circuit 428. Isolating circuit 422 can be thought of defining an isolation boundary 470, which separates an isolated side from a non-isolated side in the WCD system.

Figure 5:
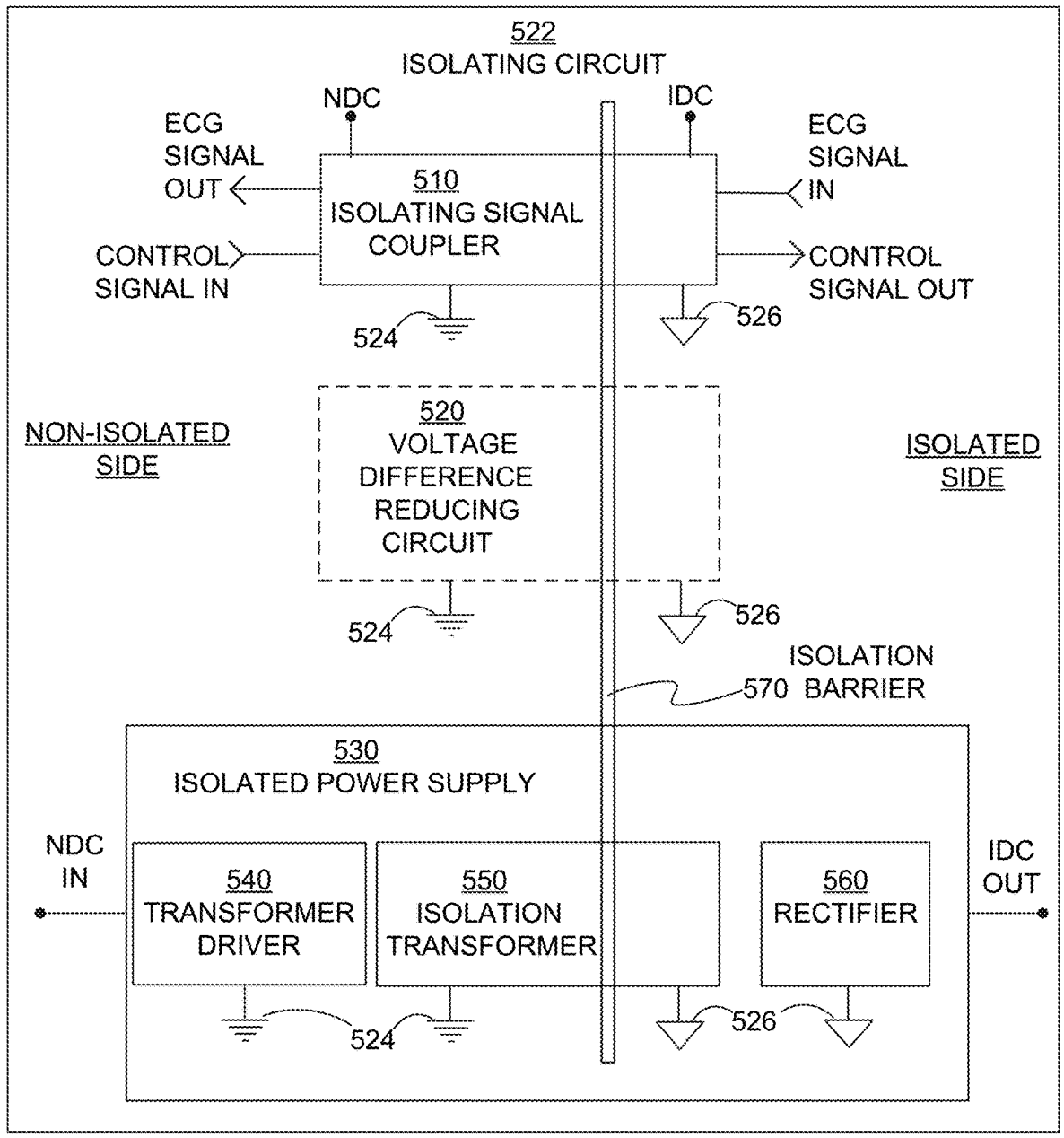
FIG. 5 is a block diagram of a sample isolating circuit of the measurement circuit of FIG. 3, made according to embodiments.

FIG. 5 is a block diagram of a sample isolating circuit for the measurement circuit of FIG. 3. Isolating circuit 522 includes an isolating signal coupler 510, an optional voltage difference reducing circuit 520, and an isolated power supply 530. Isolating circuit 522 includes a non-isolated circuit portion connected to first circuit ground 524, an isolated circuit portion connected to second circuit ground 526, which is isolated from the first circuit ground. Isolating circuit 522 includes an isolation barrier 570 electrically isolating the isolated circuit portion from the non-isolated circuit portion. Patient parameter sense port 219, such as ECG port 319 or 419, is thereby isolated from first circuit ground 524, preferably with at least 100 volts of protection across the isolation barrier. In some embodiments, the isolation barrier provides protection from the voltages applied by the defibrillator discharge circuit.

Isolating signal coupler 510 is configured to couple a signal representative of an ECG signal—the sensed patient parameter—from the isolated circuit portion of isolating circuit 522 to the non-isolated circuit portion of the isolating circuit. In an embodiment in which the signal is a digital signal, such as for isolating circuit 322 of FIG. 3, isolating signal coupler 510 includes an isolated digital data coupler configured to couple a first digital signal representative of the sensed patient parameter from ECG acquisition circuit 328 to processor 330.

Optionally, isolating signal coupler 510 is further configured to couple a second signal, such as a control signal, from processor 330 through the non-isolated circuit portion of isolating circuit 522 and the isolated circuit portion of the isolating circuit to circuits connected to the second circuit ground 526, such as the ECG acquisition circuit. Depending on the configuration of isolating signal coupler 510, signals can be coupled either direction or both directions across isolation barrier 570.

Isolating signal coupler 510 may be a digital signal coupler or an analog signal coupler. Isolation may be provided by appropriate means, such as galvanic couplers, such as provided by inductance or capacitance devices, such as an isolation transformer or an isolation capacitor, or by a non-electrical means, such as an opto-isolator. Analog signals and some digital signals are converted into a form of alternating current appropriate to cross over the isolation barrier or to cross between other isolated signal transferring components. For example, an analog signal may be converted to a binary signal using an appropriate signal-processing circuit, such as provided by an analog-to-digital converter (ADC), a switching circuit, or a pulse-width modulator. The signal form may then be converted back to its original form or further processed in its digital form, depending on the application.

The non-isolated portion of isolating signal coupler 510 receives power from a non-isolated direct-current (DC) power source NDC. The isolated portion of isolating signal coupler 510 receives power from an isolated direct-current (DC) power source IDC. Isolated power source IDC is electrically isolated from non-isolated power source NDC. Isolated power source IDC may be produced from non-isolated power source NDC, as is provided by isolated power supply 530. In some embodiments, the two power sources may be entirely independent, each with electrically separate and isolated power sources, such as batteries, and associated power supply circuits.

Optionally, isolating circuit 522 further includes a voltage-difference reducing circuit 520 configured to reduce a voltage difference between the first and second circuit grounds. First circuit ground 524 is a common reference for circuits of the defibrillator that are not isolated. Second circuit ground, not being connected to first circuit ground 524, has a reference level that floats relative to the common reference level of the first circuit ground. The voltage on the second circuit ground can thus vary compared to the first circuit ground. Voltage difference reducing circuit 520 provides a protected current path across isolation barrier 570 between the first and second circuit grounds, that does not substantially compromise the isolation between the two circuit grounds. This current path allows the voltages of the first and second circuit grounds to equalize or approach equalization. This maintains the reference potential of the first and second grounds at close to the same level. As such, even with circuit 520, embodiments attain at least substantial isolation. And, without circuit 520, isolation is even more complete.

Isolated power supply 530 is configured to transfer power from a non-isolated power source, such as power source 240 of defibrillator 200 shown in FIG. 2, to the isolated circuit portion of isolating circuit 522. Accordingly, when isolating circuit 522 is configured as shown in FIG. 3, isolated power supply 530 is configured to transfer power from non-isolated power source 240 to isolated ECG acquisition circuit 328.

The non-isolated power source produces non-isolated power supply NDC for input into isolated power supply 530. Isolated power supply 530 includes a transformer driver 540 connected to non-isolated first circuit ground 524, an isolation transformer 550 having an input side connected to non-isolated circuit ground 524 and an isolated side connected to isolated circuit ground 526, and an isolated rectifier 560 connected to isolated circuit ground 526.

Isolation transformers use varying current, such as alternating current, to transfer power. Transformer driver 540 is a switching circuit that converts the constant DC voltage of non-isolated power source NDC into an alternating power signal that is applied to isolation transformer 550. The output alternating power signal of the isolation transformer, which is electrically isolated from the input by isolation barrier 570, is then converted to an isolated direct-current power source IDC by rectifier 560.

Figure 6:
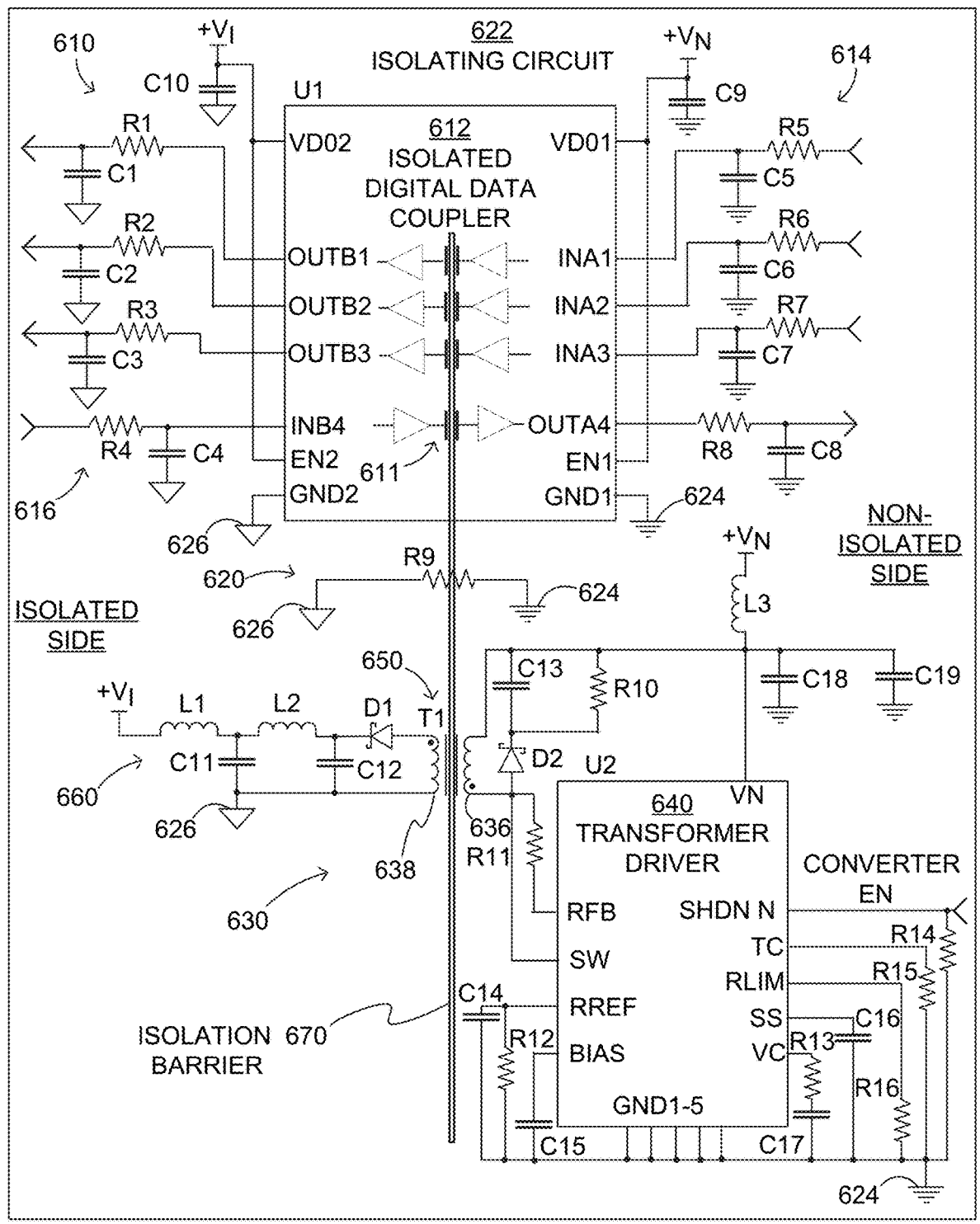
FIG. 6 is a circuit diagram of a sample of the isolating circuit of FIG. 5 as an embodiment of the measurement circuit of FIG. 3, made according to embodiments.

FIG. 6 is a circuit diagram of a sample of the isolating circuit of FIG. 5 as an embodiment of the measurement circuit of FIG. 3, made according to embodiments. In FIG. 6, the isolated side is shown at the left, while the non-isolated side is shown to the right, which is flipped compared to FIGS. 3 and 5.

In FIG. 6, isolating circuit 622 is disposed between ECG isolating circuit 328 and processor 330. Isolating circuit 622 includes an isolating signal coupler 610 including an integrated-circuit isolated digital data coupler 612 (U1) embodied as an integrated circuit configured to couple a first digital signal representative of the sensed patient parameter from the ECG acquisition circuit to the processor.

The ECG data signal is input into terminal INB4 of isolated digital data coupler 612 and output on terminal OUTA4. Isolated digital data coupler 612 is accordingly configured to couple a signal representative of the sensed patient parameter, i.e., the ECG signal, from an isolated circuit portion of isolating circuit 622, shown on the left side of isolation barrier 670 in FIG. 6, to a non-isolated circuit portion of isolating circuit 622, shown on the right side of the isolation barrier. The isolated circuit portion, connected to isolated second circuit ground 626, is isolated from first circuit ground 624. The non-isolated circuit portion is connected to first circuit ground 624.

Isolated digital data coupler 612 is further configured to couple three digital control signals from the processor to the ECG acquisition circuit. The control signals are input on circuit terminals INA1-3 and output on circuit terminals OUTB1-3. The data signals are coupled across isolation barrier 670 by respective isolating capacitors 611. Isolating signal coupler 610 includes low-pass RC input filters 614 and output filters 616 that condition the data signals received by and output by the isolated digital data coupler. While the illustrated embodiment includes bidirectional data across the isolation barrier, other embodiments include data only being transferred from the isolated to the non-isolated sides of the isolating circuit.

Isolated digital data coupler 612 receives power for the non-isolated portion of the circuit from a non-isolated voltage source $V_N$ and receives power for the isolated portion of the circuit from an isolated voltage source $V_I$.

In some embodiments, isolating circuit 622 further includes a voltage-difference reducing circuit 620 extending across isolation barrier 670 and configured to reduce a voltage difference between the isolated and non-isolated circuit grounds. In this embodiment, voltage-difference reducing circuit 620 includes a resistor R9 connecting non-isolated first circuit ground 624 to isolated second circuit ground 626. The value of resistor R9 may be selected to limit the current flowing through it. As an example, resistor R9 may have a value of 1 gigaohm. The 1-gigaohm resistor across the isolation barrier keeps the non-isolated and isolated grounds at relatively the same voltage but has no or little effect on the operation of the other circuits.

Isolating circuit 622 further includes an isolated power supply 630 configured to transfer power from the non-isolated power source to the isolated circuit portion of the isolating circuit, and thereby transfer power from the power source to the ECG acquisition circuit.

Non-isolated power source 240 is used to produce a non-isolated power source $V_N$. Isolated power supply 630 produces an isolated voltage source $V_I$ and includes an integrated-circuit transformer driver 640 (U2) connected to non-isolated first circuit ground 624. Transformer driver 640 is a switching circuit that converts the constant DC voltage of non-isolated power source $V_N$ into an alternating power signal that is applied to an isolation transformer 650.

Isolation transformer 650 includes a first winding 636 coupled to non-isolated first circuit ground 624 and a second winding 638 isolated from the first winding by isolation barrier 670 and coupled to isolated second circuit ground 626. An isolated rectifier 660 is connected to transformer second winding 638 and connected to isolated circuit ground 626. Rectifier 660 converts the alternating-current power signal produced on second winding 638 of transformer 650 to an isolated direct-current power source $V_I$.

The circuit components of isolating circuit 622 have values appropriate for the application. In some embodiments, the components have the following values:

Capacitors: C1-C8 and C14: 10 pF; C9, C10, C13, C16, and C19: 0.1 µF; C11: 47 µF; C12 and C18: 10 µF; C15: 1.0 µF; and C17: 4700 pF.

Resistors: R1-R8: 100 ohms; R9: 1 G ohms; R10: 8.08 k ohms; R11: 18.2 k ohms; R12: 8.04 k ohms; R13: 120 k ohms; R14: 100 k ohms; R15: 20.0 k ohms; and R16: 43.2 k ohms.

Inductors: L1 and L3: inductor no. BLM18EG4718N1D; and L2: 10 µH.

The inclusion of an isolation barrier between the patient-parameter ECG port, and also preferably the ECG acquisition circuitry, and the rest of the WCD system may provide advantages over a conventional non-isolated system.

1) The ECG system is isolated from the defibrillation circuit with a small capacitance between them. As such, the defibrillation circuitry and non-isolated circuit ground may not cause an imbalance in the ECG acquisition system and have little to no adverse effect on the ECG signal quality.

When there is no isolation between the ECG acquisition system, including the ECG electrodes, and the defibrillation circuitry there is a larger imbalance of capacitive load between the ECG signals and the reference used for the digitization process. compared to when there is isolation. This larger imbalance results in a larger conversion of common mode signals to differential mode signals, which corresponds to a larger noise component on the ECG signals. The lack of isolation of the ECG circuit from the general system circuitry results in a larger ground system, including printed circuit board (PCB) ground planes, ground wires, and cable shield wires. The larger ground system forms a larger capacitor with the earth, or anything electrically connected to the earth.

This capacitance varies in value as the position of the WCD ground system varies with respect to the earth or anything electrically connected to the earth.

This larger capacitance has two effects. It results in more common mode signals being converted to differential signals that degrade the ECG signals. Also, the varying nature of the larger capacitance generates more common mode signals which get converted to differential signals and further degrade the ECG signal.

2) Isolating the ECG acquisition system removes the influence of the capacitance between the non-isolated components and earth or components electrically connected to earth from the ECG acquisition system including the ECG acquisition circuit, ECG port, and ECG electrodes. The capacitance to earth is limited to the smaller isolated ground system and the earth. This can be made considerably smaller than the complete WCD system ground system. This may result in the ECG signal being degraded significantly less by having a much smaller capacitance between the isolated ground and earth as compared to the non-isolated WCD system.

3) During normal operation of a WCD system having isolated ECG circuits, patient leakage currents from the ECG electrodes are limited to being produced by components of the isolated part of the system and do not have a return path through the defibrillation electrodes. The isolated ECG acquisition system is a simpler system and is more easily designed to limit patient leakage currents in ways that have little impact on the entire WCD system. The non-isolated system has additional leakage paths between the power source or the earth and the patient. These additional paths should be identified and carefully designed so as to maintain safe operation while attached to the patient.

4) The isolating circuitry reduces the coupling between electrical noise sources on the non-isolated side and the ECG acquisition system. This results in higher ECG signal quality.

In embodiments, such as is described with reference to FIGS. 1-3, 5, and 6, the isolated circuits form an isolation zone that includes an isolated power supply and an isolated digital data coupler for transferring information between the isolated ECG acquisition system and the non-isolated parts of the WCD system. The non-isolated WCD system generally includes a processor for both controlling the ECG acquisition system and receiving ECG and other data from this system. Many of the benefits of the isolated ECG acquisition system may be realized by using an isolation barrier providing an isolation voltage as low as around 100 volts. However, the isolation barrier preferably provides enough isolation to not break down during the defibrillation electrical discharge.

Other embodiments, such as is described with reference to FIGS. 1, 2, 4, and 5, can include an analog isolating signal coupler that transfers the analog signals from the isolated section to the non-isolated section of the WCD system, which then includes the ECG acquisition circuit.

A person skilled in the art will be able to practice the present invention in view of this description, which is to be taken as a whole. Details have been included to provide a thorough understanding. In other instances, well-known aspects have not been described, in order to not obscure unnecessarily this description. Plus, any reference to any prior art in this description is not, and should not be taken as, an acknowledgement or any form of suggestion that such prior art forms parts of the common general knowledge in any country or any art.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

What is claimed is:

1. A wearable cardioverter defibrillator (WCD) system, comprising:
   a support structure configured to be worn by a patient;
   a patient parameter sense port;
   Electrocardiogram (ECG) electrodes configured to be coupled to the patient parameter sense port and to sense an ECG signal of the patient;
   a first circuit ground;
   a second circuit ground electrically isolated from the first circuit ground;
   a power source connected to the first circuit ground;
   an energy storage module electrically connected to the first circuit ground and configured to be charged from the power source to store an electrical charge;
   a discharge circuit electrically coupled to the energy storage module;
   a measurement circuit configured to render ECG data from the ECG signal received at the patient parameter sense port as sensed by the ECG electrodes, the measurement circuit including an isolating circuit directly coupled to both the first circuit ground and to the second circuit ground, the isolating circuit configured to electrically isolate the patient parameter sense port from the first circuit ground; and
   a processor electrically connected to the first circuit ground, operatively coupled to the measurement circuit, and configured to:
   determine from the ECG data whether or not a shock criterion is met, and
   control the discharge circuit to discharge the stored electrical charge through the patient while the support structure is worn by the patient responsive to the shock criterion being met,
   wherein the isolating circuit comprises an isolated side that includes an isolated circuit portion connected to the second circuit ground isolated from the first circuit ground and a non-isolated side that includes a non-isolated circuit portion connected to the first circuit ground.

2. The WCD system of claim 1, wherein the measurement circuit includes an ECG acquisition circuit coupled to the patient parameter sense port and the isolating circuit, the ECG acquisition circuit being configured to detect the ECG signal.

3. The WCD system of claim 2, in which the isolating circuit includes an isolated digital data coupler configured to couple a first digital signal representative of the sensed patient parameter from the ECG acquisition circuit to the processor.

4. The WCD system of claim 3, in which the isolated digital data coupler is configured to couple a second digital signal from the processor to the ECG acquisition circuit.

5. The WCD system of claim 3, in which the isolating circuit further includes an isolated power supply configured to transfer power from the power source to the ECG acquisition circuit.

6. The WCD system of claim 2, in which the isolating circuit includes an isolating signal coupler configured to couple a first parameter signal representative of the sensed patient parameter from the patient parameter sense port to the ECG acquisition circuit.

7. The WCD system of claim 2, in which the ECG acquisition circuit couples the isolating circuit to the patient parameter sense port, and the ECG acquisition circuit is connected to the second circuit ground and isolated from the first circuit ground.

8. The WCD system of claim 1, in which the isolating circuit includes an isolation barrier electrically isolating the patient parameter sense port from the first circuit ground with at least 100 volts of protection across the isolation barrier.

9. The WCD system of claim 1, wherein the isolating circuit further includes a voltage-difference reducing circuit configured to reduce a voltage difference between the first circuit ground and the second circuit grounds.

10. The WCD system of claim 9, in which the voltage-difference reducing circuit includes a resistor connecting the first circuit ground to the second circuit ground.

11. The WCD system of claim 1, in which the isolating circuit includes an isolating signal coupler configured to couple a signal representative of the sensed patient parameter from the isolated circuit portion of the isolating circuit to the non-isolated circuit portion of the isolating circuit, the isolated circuit portion is isolated from the first circuit ground, and the non-isolated circuit portion is connected to the first circuit ground.

12. The WCD system of claim 11, in which the isolating circuit further includes an isolated power supply configured to transfer power from the power source to the isolated circuit portion of the isolating circuit.

13. The WCD system of claim 12, wherein the isolated power supply includes an isolation transformer having a first winding coupled to the first circuit ground and a second winding isolated from the first winding and coupled to the second circuit ground.

* * * * *